United States Patent [19]

Mattern

[11] 4,033,975
[45] July 5, 1977

[54] PROCESS FOR THE PRODUCTION OF 2-AMINO-3-HYDROXYPYRIDINE DERIVATIVES

[75] Inventor: Günter Mattern, Liestal, Switzerland

[73] Assignee: Ciba-Geigy Corporation, Ardsley, N.Y.

[22] Filed: May 10, 1976

[21] Appl. No.: 684,692

[30] Foreign Application Priority Data

May 13, 1975 Switzerland .................... 6158/75

[52] U.S. Cl. .......................... 260/296 R; 424/263; 260/297 B; 260/297 P; 260/297 R
[51] Int. Cl.² ...................................... C07D 213/61
[58] Field of Search ............................. 260/296 R

[56] References Cited

UNITED STATES PATENTS

| 1,778,784 | 10/1930 | Rath | 260/296 R |
| 3,355,456 | 11/1967 | Sexton | 260/297 |
| 3,579,528 | 5/1971 | Haszeldine et al. | 260/296 R X |
| 3,849,429 | 11/1974 | Boudakian | 260/296 R |

FOREIGN PATENTS OR APPLICATIONS 2,245,363  3/1973  Germany .................. 260/296 R X

OTHER PUBLICATIONS

Klingsberg, Pyridine and Derivatives, Part II, pp. 334 to 337, Interscience Publishers, Inc. NY (1961).
Klingsberg, Pyridine and Derivatives, vol. 3, pp. 571 to 576, Interscience Publishers (1962).
Yamamoto et al., Chemical Abstracts, vol. 46, cols. 8108 to 8109 (1952).

*Primary Examiner*—John D. Randolph
*Attorney, Agent, or Firm*—Harry Falber

[57] ABSTRACT

2-Amino-3-hydroxy-5-chloropyridine and 2-amino-3-hydroxy-5-bromopyridine are produced by selective hydrolysis of corresponding 2-amino-3,5-dihalopyridines.

8 Claims, No Drawings

PROCESS FOR THE PRODUCTION OF 2-AMINO-3-HYDROXYPYRIDINE DERIVATIVES

The present invention relates to a novel process for the production of 2-amino-3-hydroxypyridine derivatives of formula I

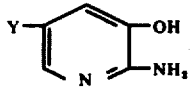

(I)

wherein
Y represents chlorine or bromine.

The 2-amino-3-hydroxypyridine derivatives of formula I are valuable intermediates for producing pesticidal compositions, pharmaceutics and dyes. Of particular importance is 2-amino-3-hydroxy-5-chloropyridine, from which is obtained, by reaction with phosgene, the corresponding 6-chloro-oxazolo-[4,5-b]-pyridin-2(3H)-one, which can be converted, by subsequent reaction with formaldehyde and thionyl chloride, firstly into the corresponding 3-chloromethyl-6-chloro-oxazolo-[4,5-b]-pyridin-2(3H)-one, from which can be produced, by reaction with alkali dialkylphosphates or ammonium dialkylphosphates or alkali dialkylthiophosphates or ammonium dialkylthiophosphates, phosphoric acid esters of the formula

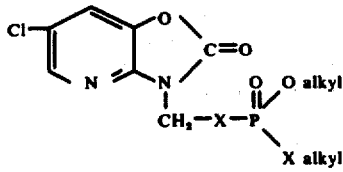

wherein X represents oxygen or sulphur. These phosphoric acid esters have an excellent insecticidal action (see U.S. Pat. No. 3,808,218).

Compounds of formula I can be produced by a known process comprising firstly the coversion of a 3,5-dihalogenopyridine with sodium ethylate into a 3-ethoxy-5-halogenopyridine and of this into a 3-hydroxy-5-halogenopyridine, and subsequently the introduction of an amino group in the 2-position by reaction with sodium amide in toluene according to Tschitschibabin (H. J. den Hertog et al., Recuil des Travaux Chimiques des Pays-Bas, 69, 1281 (1950), 70, 185 (1951)).

According to a further known process, 3-hydroxypyridine is firstly nitrated in the 5-position, the product obtained is reduced to the corresponding 5-amino compound, this is diazotised and the resulting product is reacted with a copper-1-halide to a corresponding 3-hydroxy-5-halogenopyridine, into which is then introduced again in the 2-position an amino group (DT-OLS 2,245,363). The 3-hydroxypyridine used as starting material in this process can be produced by the process described in the German 'Auslegeschrift' No. 1,134,376, or by the process described in the British patent specification No. 862,581.

The production of compounds of formula I by the aforementioned known processes is not only complicated but also unsatisfactory in that only moderate yields are obtained.

It has now been found that the compound of formula I can be produced appreciably more simply and in good yields by reacting a 2-amino-3,5-dihalogenopyridine of formula II

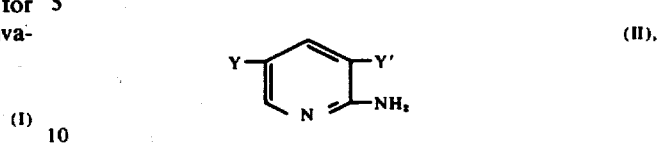

wherein the two symbols Y and Y' can be identical or different and represent chlorine or bromine, at 140° to 240° C in the presence of a base with water.

The reaction medium used for the process of the invention can be water or a mixture of water and an organic solvent. Suitable organic solvents are, in particular, high-boiling alcohols, especially ethylene glycol and ethylene glycol alkyl ether having 1–4 carbon atoms in the alkyl group, especially ethylene glycol monoethyl ether.

Suitable bases are alkali metal hydroxides and alkaline-earth metal hydroxides, such as sodium hydroxide, potassium hydroxide and calcium hydroxide, or basically reacting salts such as alkali acetates and alkali carbonates. It is advantageous to perform the reaction in the presence of copper powder and/or in the presence of copper salts. Copper salts usable according to the invention are, in particular, the sulphate, the chloride and the acetate.

The starting materials of formula II can be obtained by halogenating 2-aminopyridine in aqueous mineral acid, e.g. sulphuric acid or hydrochloric acid. For example, 2-aminopyridine is dissolved in concentrated hydrochloric acid and the solution is chlorinated firstly with slight cooling and subsequently with heating to 40° to 70° C, whereby 2-amino-3,5-dichloropyridine is obtained. In order to obtain 2-amino-3-bromo-5-chloropyridine, 2-aminopyridine is firstly chlorinated in the presence of hydrochloric acid, with cooling, to 2-amino-5-chloropyridine, the calculated amount of an alkali bromide is then added and chlorine gas is further introduced.

In the temperature range of 140° to 240° C in which the process of the invention is performed, the preferred temperatures are between 150° and 210° C.

The molar ratio of base to 2-amino-3,5-dihalogenopyridine can be between 1:1 and 10:1. The best results are obtained when the molar ratio of base to pyridine derivative is between 4:1 and 8:1.

It is possible by means of the process of the invention to produce compounds of formula I in a simple manner and in good yields. The process of the invention can be used with particular advantage to produce 6-chloro-oxazolo[4,5-b]pyridin-2-(3H)-one, from the 1-methylol compound of which there are derived phosphoric acid esters and thiophosphoric acid esters having an excellent insecticidal action.

The process of the invention is further illustrated by the following Examples.

EXAMPLE 1

A mixture of 12 parts of potassium hydroxide (85%), 200 parts of water, 10.4 parts of 2-amino-3-bromo-5-chloropyridine and 0.5 part of copper powder is stirred under nitrogen in an autoclave for 10 hours at 170° C. The aqueous solution is afterwards neutralised with concentrated hydrochloric acid and the wateris largely evaporated off. While still moist the residue is extracted in the hot state twice with ethyl acetate. The combined extracts are purified with active charcoal, and the solvent is then evaporated off to leave 5 parts (70% of theory) of 2-amino-3-hydroxy-5-chloropyridine, m.p. 196°–201° C.

To produce 2-amino-3-bromo-5-chloropyridine, 30 parts of chlorine are introduced in the course of 50 minutes, with slight cooling, into a solution of 37.6 parts of 2-aminopyridine in 160 parts of concentrated hydrochloric acid (36%). A solution of 53 parts of potassium bromide in 50 parts of water is then added, and a further 30 parts of chlorine are introduced within one hour at a temperature of about 35° C, whereby finally a light-yellow precipitate occurs. The mixture obtained is stirred for a further 30 minutes. The solution is afterwards poured on to ice, and the free halogen still present is removed by the addition of sodium bisulphite solution. There is now added, with ice-cooling, a solution of 95 parts of sodium hydroxide in 190 parts of water. The resulting beige-coloured precipitate is filtered off with suction, washed with ice-water and dried at 30° to 40° C in a water-jet vacuum. There are obtained 74 parts (90% of theory) of 2-amino-3-bromo-5-chloropyridine, m.p. 78°–79° C.

EXAMPLE 2

A mixture of 20 parts of 2-amino-3,5-dichloropyridine, 160 parts of glycol, 80 parts of potassium hydroxide, 1 part of copper powder and 3 parts of diethylene glycol dimethyl ether is stirred under nitrogen for 5 hours at 150°–160° C. The cooled solution is neutralised with conc. hydrochloric acid, saturated with sodium chloride and extracted twice in the warm state with ethyl acetate. The combined extracts are filtered through Hyflo, dried over magnesium sulphate and purified with active charcoal. The solvent is evaporated off to leave 12.3 parts (70% of theory) of 2-amino-3-hydroxy-5-chloropyridine, m.p. 198°–201° C.

To produce 2-amino-3,5-dichloropyridine, 30 parts of chlorine are introduced in the course of 30 minutes, with slight cooling, into a solution of 37.6 parts of 2-aminopyridine in 160 parts of concentrated hydrochloric acid. The temperature is then raised to 50° to 60° C and a further 60 parts of chlorine are introduced during 6 hours. After completion of the chlorine addition, the solution is poured onto ice, and the chlorine still present is removed with sodium bisulphite. There is then added a solution of 95 parts of sodium hydroxide in 150 parts of water, whereupon 2-amino-3,5-dichloropyridine precipitates. It is filtered off, washed with ice-water and dried at room temperature in water-jet vacuum. There are obtained 58.5 parts (90% of theory) of 2-amino-3,5-dichloropyridine, m.p. 77°–79° C.

EXAMPLE 3

6 Parts of 2-amino-3,5-dibromopyridine are mixed with 20 parts of potassium hydroxide (85%), 3 parts of diethylene glycol dimethyl ether, 0.3 part of copper-bronze and 45 parts of glycol, and the whole is then stirred under nitrogen for 7 hours at 145°–150° C. The cooled solution is neutralised with concentrated hydrochloric acid, saturated with sodium chloride and extracted three times in the warm state with ethyl acetate. The organic layer is filtered through Hyflo, dried with sodium sulphate and purified with active charcoal. After removal of the solvent by evaporation, the semi-solid substance is stirred well with a small amount of water and then filtered. After drying in vacuo at 40° C, the residue contains 1.8 parts (40% of theory) of 2-amino-3-hydroxy-5-bromopyridine, m.p. 204°–208° C.

EXAMPLE 4

A mixture of 6.5 parts of 2-amino-3,5-dibromopyridine, 12 parts of potassium hydroxide (85%), 0.5 part of copper powder and 100 parts of water is stirred under nitrogen in an autoclave for 10 hours at 170° C. The dark-coloured solution is neutralised with concentrated hydrochloric acid, saturated with sodium chloride and extracted three times in the warm state with an ethyl acetate/tetrahydrofuran mixture (9:1). The combined organic extracts are filtered through Hyflo, dried with sodium sulphate and filtered. After the solvent has been evaporated off, the residue is taken up in a small amount of hot ethyl acetate and chromatographed through silica gel. After removal of the ethyl acetate, there are obtained 2.2 parts (46.3% of theory) of 2-amino-3-hydroxy-5-bromopyridine, m.p. 205°–208° C.

EXAMPLE 5

A mixture of 5 parts of 2-amino-3-chloro-5-bromopyridine, 20 parts of potassium hydroxide (85%), 3 parts of diethylene glycol dimethyl ether, 0.3 part of copper-bronze and 40 parts of glycol is stirred under nitrogen for 7 hours at 170°–175° C. After cooling, the dark-coloured solution is neutralised with concentrated hydrochloric acid, saturated with sodium chloride and extracted twice in the warm state with ethyl acetate/tetrahydrofuran (9:1). The organic layer is extracted by shaking with a saturated sodium chloride solution; the ethyl acetate phase is then filtered through Hyflo, dried with magnesium sulphate and purified with active charcoal. The clear yellow solution is concentrated almost to dryness and chromatographed through a short silica-gel column with ethyl acetate/cyclohexane (2:1). The yield is 2 parts of 2-amino-3-hydroxy-5-bromopyridine, m.p. 204°–207° C (44.1% of theory).

To produce 2-amino-3-chloro-5-bromopyridine, chlorine is slowly introduced in the course of 8 hours at about 50° C into a solution of 25 parts of 2-amino-5-bromopyridine in 70 parts of concentrated hydrochloric acid. After complete reaction, the solution is poured into ice-water, and the unreacted chlorine is decomposed with sodium bisulphite. Whilst ice is added, the solution is adjusted at 15° with 30% sodium hydroxide solution to pH 8 and subsequently stirred for one hour; the precipitate is then filtered off and washed with water. Recrystallisation from cyclohexane yields 28.5 parts (95.4% of theory) of 2-amino-3-chloro-5-bromopyridine in the form of white needles, m.p. 94°–96° C.

EXAMPLE 6

Phosgene is introduced at 40°–50° C, after the addition of 20 parts of pyridine, into a solution of 10 parts of 2-amino-3-hydroxy-5-chloropyridine in 200 parts of chloroform, and stirring is maintained for 1 hour at room temperature; the chloroform and the pyridine are evaporated off in a water-jet vacuum, and ice-water is added to the residue. The precipitate is filtered off and dried at 40°–50° C in vacuo. There are obtained 10 parts of 6-chloro-oxazolo[4,5-b]pyridin-2-(3H)-one (85% of theory), m.p. 184°–186° C.

8 parts of 38% formaldehyde solution and 25 parts of 2N hydrochloric acid are added to a solution of 8.5 parts of 6-chlorooxazolo-[4,5-b]-pyridin-2-(3H)-one in 60 parts of water, and the whole is stirred for 4 hours at 50° to 60° C. After cooling with ice, filtration is performed and the residue is washed with ice water. There are obtained 8.5 parts of 3-hydroxymethyl-6-chloro-oxazolo [4,5-b]pyridin-2-(3H)-one (85% of theory), m.p. 137°–139° C.

39 Parts of thionyl chloride are added dropwise, in a manner ensuring that the internal temperature does not exceed 50° C, to a solution of 45 parts of 3-hydroxymethyl-6-chloro-oxazolo[4,5-b]pyridin-2-(3H)-one in 200 parts of toluene; and the whole is stirred for a further 4 hours at 40°–50° C. The resulting solution is subsequently freed from gases in a water-jet vacuum, and sufficient toluene is evaporated off to leave a crystal sludge that can still just be stirred. After the addition of 100 parts of hexane, filtration is carried out and the filter cake is washed twice with cold hexane. There are obtained 40 parts of 3-chloromethyl-6-chloro-oxazolo[4,5-b]pyridin-2-(3H)-one (83% of theory), m.p. 105°–107° C.

7.2 Parts of ammonium-thio-0,0-dimethylphosphate are added to a solution of 30 parts of 3-chloromethyl-6-chloro-oxazolo-[4,5-b]-pyridin-2(3H)-one in 40 parts of methanol. The mixture is stirred for 10 minutes at 55° to 65° C; it is then cooled to 40° C, filtered and the filtrate is concentrated to dryness in a water-jet vacuum at 30° to 40° C. After recrystallisation of the residue from methanol, there are obtained 10.5 parts of S-[6-chloro-oxazolo-[4,5-b]pyridin-2(3H)-on-3-yl-methyl]-0,0-dimethylthiophosphate (64% of theory), m.p. 89°–91° C.

I claim:

1. Process for the production of 2-amino-3-hydroxypyridine derivatives of formula I

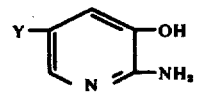

wherein

Y represents chlorine or bromine, which process comprises reacting a 2-amino-3,5-dihalogenopyridine of formula II

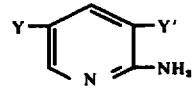

in which the two symbols Y and Y' can be identical or different and represent chlorine or bromine, at 140°–240° C in the presence of a base with water.

2. Process according to claim 1, wherein the solvent used is water.

3. Process according to claim 1, wherein the reaction is performed in ethylene glycol or in an ethylene glycol monoalkyl ether having 1 to 4 carbon atoms in the alkyl group.

4. Process according to claim 1, wherein the reaction is performed in ethylene glycol monoethyl ether.

5. Process according to claim 1, wherein the base used is an alkali metal hydroxide or alkaline-earth metal hydroxide.

6. Process according to claim 1, wherein the base used is an alkali acetate or alkali carbonate.

7. Process according to claim 1, wherein the reaction is performed in the presence of copper powder and/or in the presence of copper salts.

8. Process according to claim 1, wherein the molar ratio of base to 2-amino-3,5-dihalogenopyridine of formula II is between 4:1 and 8:1.

* * * * *